(12) United States Patent
Kisters et al.

(10) Patent No.: US 6,331,569 B1
(45) Date of Patent: Dec. 18, 2001

(54) PREPARATION FOR IMPROVING HAIR GROWTH, THE SKIN STRUCTURE AND/OR NAIL REGENERATION

(76) Inventors: Friedrich Kisters, Seeblickstrasse 34-36, CH-8280 Kreuzlingen 4 (CH); Reinhold Nöfer, Ulmerstrasse 2, D-87751 Heimertingen (DE); Günther Kessler, deceased, late of Tettnang (DE); by Wiltrud Elfriede Bichsel-Kessler, legal representative, Hofkammerstrasse 15, 80069 Tettnang (DE); by Gerlinde Margarete Kisters, legal representative, Seeblickstrasse 34, CH-8280 Kreuzlingen (DE); by Ingrid Hildegund Kessler-Wetzig, legal representative, Heimstrasse 15, 89075 Ulm (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/101,817
(22) PCT Filed: Dec. 31, 1996
(86) PCT No.: PCT/CH96/00466
§ 371 Date: Jun. 22, 1999
§ 102(e) Date: Jun. 22, 1999
(87) PCT Pub. No.: WO97/25972
PCT Pub. Date: Jul. 24, 1997
(Under 37 CFR 1.47)

(30) Foreign Application Priority Data

Jan. 17, 1996 (WO) .................................. PCT/CH96/00024

(51) Int. Cl.$^7$ ...................................................... A61K 31/195
(52) U.S. Cl. ............................................. 514/561; 514/880
(58) Field of Search ..................................... 514/561, 880

(56) References Cited

U.S. PATENT DOCUMENTS 5,198,465   3/1993   Dioguardi .

FOREIGN PATENT DOCUMENTS

| 36 37 992 | 5/1988 | (DE) . |
| 42 43 362 | 6/1994 | (DE) . |
| 42 43 363 | 6/1994 | (DE) . |
| 2 268 871 | 1/1994 | (GB) . |
| 96/27371 | 9/1996 | (WO) . |

OTHER PUBLICATIONS

CA 125: 220495, Aug. 6, 1996.*
WPIDS AN 1995–057299, Dec. 6, 1994.*
WPIDS AN 1996–368101, Jul. 9, 1996.*

* cited by examiner

*Primary Examiner*—Marianne M. Cintins
(74) *Attorney, Agent, or Firm*—Browdy and Neimark

(57) ABSTRACT

To improve the quantitative and qualitative hair growth, skin structure and/or nail regeneration, a mixture of proline and carrier substances is used, which may additionally contain at least one of the four amino acids valine, leucine, isoleucine and/or glycine. The mixture is prepared for oral administration. The mixture may contain, as additional additives, ATP, biotin, cysteine, lysine, methionine, and others. The preparation may furthermore have a positive effect on the stamina, muscle build-up, brain performance, fat catabolism, blood fat and blood sugar values and the firmness of the connective tissue.

11 Claims, 6 Drawing Sheets

| Patient No. | 0th Month | 1st Month | 2nd Month | 3rd Month | 4th Month | 5th Month | 6th Month |
|---|---|---|---|---|---|---|---|
| 1 | 120 | 110 | 120 | 110 | 85 | 80 | 60 |
| 2 | 110 | 110 | 110 | 105 | 90 | 70 | 55 |
| 3 | 130 | 120 | 110 | 115 | 75 | 80 | 45 |
| 4 | 135 | 110 | 100 | 70 | | | |
| 5 | 150 | 105 | 85 | 65 | | | |
| 6 | 140 | 130 | 110 | 60 | | | |
| 7 | 110 | 90 | 70 | 50 | | | |
| 8 | 125 | 120 | 75 | 45 | | | |
| 9 | 140 | 110 | 80 | 40 | | | |
| 10 | 135 | 125 | 105 | 70 | | | |
| 11 | 115 | 115 | 90 | 55 | | | |
| 12 | 120 | 110 | 110 | 80 | | | |
| 13 | 120 | 90 | 70 | 35 | | | |
| 14 | 120 | 125 | 80 | 60 | | | |
| 15 | 140 | 105 | 75 | 50 | | | |

FIG. 1

| Patient No. | 0th Month anagenic | 3rd Month | 6th Month |
|---|---|---|---|
| 1 | 68 | 70 | 82 |
| 2 | 70 | 68 | 80 |
| 3 | 64 | 66 | 82 |
| 4 | 68 | 80 | |
| 5 | 64 | 78 | |
| 6 | 70 | 80 | |
| 7 | 76 | 82 | |
| 8 | 72 | 80 | |
| 9 | 68 | 78 | |
| 10 | 74 | 78 | |
| 11 | 74 | 82 | |
| 12 | 74 | 78 | |
| 13 | 72 | 84 | |
| 14 | 70 | 84 | |
| 15 | 70 | 80 | |

FIG. 3

| Patient No. | 0th Month anagenic | 3rd Month | 6th Month |
|---|---|---|---|
| 1 | 4 | 6 | 2 |
| 2 | 6 | 4 | 0 |
| 3 | 6 | 6 | 2 |
| 4 | 6 | 2 | |
| 5 | 8 | 0 | |
| 6 | 6 | 2 | |
| 7 | 4 | 0 | |
| 8 | 6 | 2 | |
| 9 | 8 | 0 | |
| 10 | 6 | 2 | |
| 11 | 4 | 0 | |
| 12 | 4 | 0 | |
| 13 | 4 | 2 | |
| 14 | 2 | 2 | |
| 15 | 4 | 0 | |

FIG. 5

PREPARATION FOR IMPROVING HAIR GROWTH, THE SKIN STRUCTURE AND/OR NAIL REGENERATION

This is a 371 of PCT/CH96/00466 filed Dec. 31, 1996.

The present invention relates to a preparation for the improvement of the hair growth and/or nail regeneration in accordance with the generic part of claim 1.

This invention relates to a dietetic preparation for the support and/or regulation of the various energy metabolism pathways in the human body, for the specific purpose of improving the synthesis of structural proteins. An oral administration of the preparation in accordance with the present invention therefore has a positive effect, particularly on the hair growth and hair structure.

The term metabolism denotes the entirety of the chemical conversions in an organism that are necessary to maintain the life processes. These are related to the intake, deposit, conversion and catabolism, as well as the elimination of substances for the preservation and/or development of the body substance and, of course, also for the production of energy.

The terms energy metabolism or operating metabolism are used to refer to the conversion of endogenic materials for the production of energy: as heat energy to maintain the body heat, as mechanical energy for the work performed by the organs and muscles, as chemical energy for the synthesis of species-characteristic proteins, fats, glycogen, polynucleotides, high-energy phosphate compounds, to generate electrical potentials, for osmotic work, and so on. Closely connected to the energy metabolism is the building or preservation metabolism, which supports both, the production (biogenesis) of necessary cell components from simple elements, and the catabolism of polymolecular materials to low-molecular substances, which are either used for synthesis reactions elsewhere in the organism or eliminated.

In the energy metabolism—but not in the building metabolism—the energy suppliers, such as carbohydrates, protein and fats, can substitute for each other to a certain degree since they are ultimately converted into energy through similar catabolism pathways. Of particular importance in this context are the amino acids. By amino acids one understands the 20 (proteinogenic) L-aminocarbonic acids, which take part in the synthesis of proteins. Plants are able to synthesize all amino acids from simpler preliminary stages. Humans and animals, by contrast, can produce only the so-called non-essential amino acids alanine, asparagine, aspartic acid, glutamine, glutaminic acid, hydroxy-L-proline, proline, glycine and serine. The essential amino acids isoleucine, leucine, lysine, methionine, phenylalanine, ornithine, threonine, tryptophane and valine must be absorbed with the food. Arginine and histidine, which must be supplied externally only during growth phases and if deficiency symptoms are present, are considered semi-essential. Cysteine and tyrosine, which can be synthesized from the essential amino acids methionine and phenylalanine, form a special group. The most important function of the amino acids is that of components for the biosynthesis of proteins; if essential amino acids are absent in the food, the protein synthesis, among other things, starts to slow down, and life-threatening deficiency symptoms may result as a further consequence.

The physiological synthesis and catabolism of the amino acids occurs via the catabolic products of the glycolysis and alpha-ketonic acids, of which 2-oxoglutaric acid and oxalacetic acid are members of the citric acid cycle. Through them, the metabolism of amino acids is linked with that of fats and carbohydrates. Regarding their catabolic products, one differentiates between glucogenic amino acids, which supply intermediates of the citric acid cycle or pruvic acid, and ketogenic amino acids, which cannot be used for the glucose synthesis, since their catabolism produces ketones such as acetoacetic acid. Since the amino acids are also of great importance as nutrients, there are various specific cellular transport systems that adjust the intake of amino acids through the membrane.

The normally balanced ratio of absorption, conversion, catabolism and elimination of the various substances, above all also in the case of the amino acid metabolism, can be unbalanced by various disorders. Examples for these are diabetes, lipidoses, gout, hyperthyreosis, rachitis, phenylketonuria, infections and many other disorders, which may be acquired or inherited. Disorders which are caused by stress and environmental factors (e.g., all sorts of toxins), as well as by medication should, of course, also not be overlooked.

The results are oftentimes a loss of energy, tiredness, muscle atrophy, reduced brain performance, impaired potency, or changes in the blood fat and blood sugar values. A particularly striking external indication for such a disorder is the non-hormone based, i.e., non-testosterone based hair loss, which can manifest itself as the so-called "effluvium" or also as "alopecia", in which hair loss occurs, which may be concentrated in one area, scattered, or complete baldness. Regarding the prognosis, one differentiates between reversible and irreversible alopecia, whereby the irreversible alopecia is characterized by a destruction and/or an absence of the potential to grow hair. The preparation claimed in the present application had the surprising effect of reversing the course of the alopecia in 2 of 10 cases, and in 6 cases stopped the alopecia after a 2-month treatment. In one case a reduction of the hair loss was registered and in 2 further cases no effect was seen. This means that a healing process was found in 7 of 10 patients within 2 months, which is an unequaled healing success for alopecia.

The human hair goes through a life cycle comprising three phases, i.e., the anagenic or growth phase, the katagenic or transitional phase, and the telogenic or resting phase. Under normal conditions 80 to 85% of the hair is in the anagenic phase and 15 to 20% in the transitional and/or resting phase. The anagenic phase is the period of active hair growth and lasts approx. 3 to 5 years. The katagenic phase is a transitional phase between active growth and resting phase and lasts about 1 to 2 weeks. The following telogenic phase lasts 3 to 4 months. At this time the growth stops and the hair may be cast off, after which new hair growth begins. If increased hair loss occurs in a patient, this may be due to the fact that a larger portion than the above-mentioned 15 to 20% of the hair is present in the telogenic phase. A further cause is to be seen in a reduction in the number of hair follicles, which amount to approximately 500 follicles per square centimeter in a person with normal hair growth and decrease in number if hair growth disorders are present.

A multiplicity of the most diverse preparations is available commercially, which are used both externally, in the form of cosmetics such as hair tonics, hair shampoo and the like, and as preparations for internal use, i.e., orally administered preparations of greatly differing compositions, which frequently have undesired side effects.

It is already known that the administration of a number of amino acids can contribute to strengthening the human organism, and that certain combinations of various amino acids lead to a strengthening of the muscles, build-up of the brain, stimulation of the hair growth etc. In particular, a mixture of the amino acids leucine, isoleucine and valine has been sold as a hair-restorer, either alone or in combination, e.g., with fructose and/or glucose. However, in the persons tested within the framework of the present invention, this preparation did not have an actual effect.

A multiplicity of preparations is recommended for external application, for purely cosmetic purposes. So far it has not been possible to prove any significant absorption of nutrition through the skin; an external use of amino acids, vitamins, trace elements, proteins, fats and fatty acids is thus likely without benefit. An external treatment can generally improve the quality of already existing hair, but will not improve its growth. Growth-related damage and disorders can be treated in a meaningful way only through oral administration.

U.S. Pat. No. 5,198,465 by Dioguardi describes a composition which is based on amino acids and intended to prevent malformations during the collagen synthesis. The described preparation is essentially composed of proline, glycine, lysine and vitamin C, whereby the amino acids are always administered in the same weight ratios (10:50:10), regardless of whether the preparation is given orally or applied externally.

The unexamined German patent application DE 36 37 992 relates to a hair-restorer, whose active substances are based on torula yeast. This type of yeast contains almost all amino acids in addition to a great number of vitamins and trace elements. The effect of this preparation is based on "the mutually strengthening interaction" of the individual components.

The unexamined German patent applications DE 42 43 362 and DE 42 43 363 relate to a quercetin-containing agent, which additionally also contains proline, lysine, ascorbic acid and one or several of the amino acids valine, leucine and isoleucine. This agent is used for the treatment of dry skin, the neuroendocrinium (only DE 42 42 362) and the immune system. The agent can be administered both orally and parenterally, as well as topically, i.e., externally, and the above-listed ingredients are administered in fixed quantities, without consideration of the physiological condition of the individual patient.

GB 2 268 871 uses a combination of various vitamins, minerals and trace elements as a nutritional supplement. The preparation has many diverse applications, such as prostrate and menopause-related discomfort, to support the potency and enhance the firmness of the skin. The composition of the preparation is based on the ailments to be treated, but not on the respective constitution of the individual patient.

BRIEF DESCRIPTION OF THE FIGURES

FIG. 1 and FIG. 2 show that daily hair loss was reduced using the four amino acids.

FIG. 3 and FIG. 4 show that hair growth phases shifted from the ketagenic and telogenic phase to the anagenic phase using the four amino acids.

FIG. 5 and FIG. 6 show that the structure of the hair shafts improved using the four amino acids.

Figure 2:
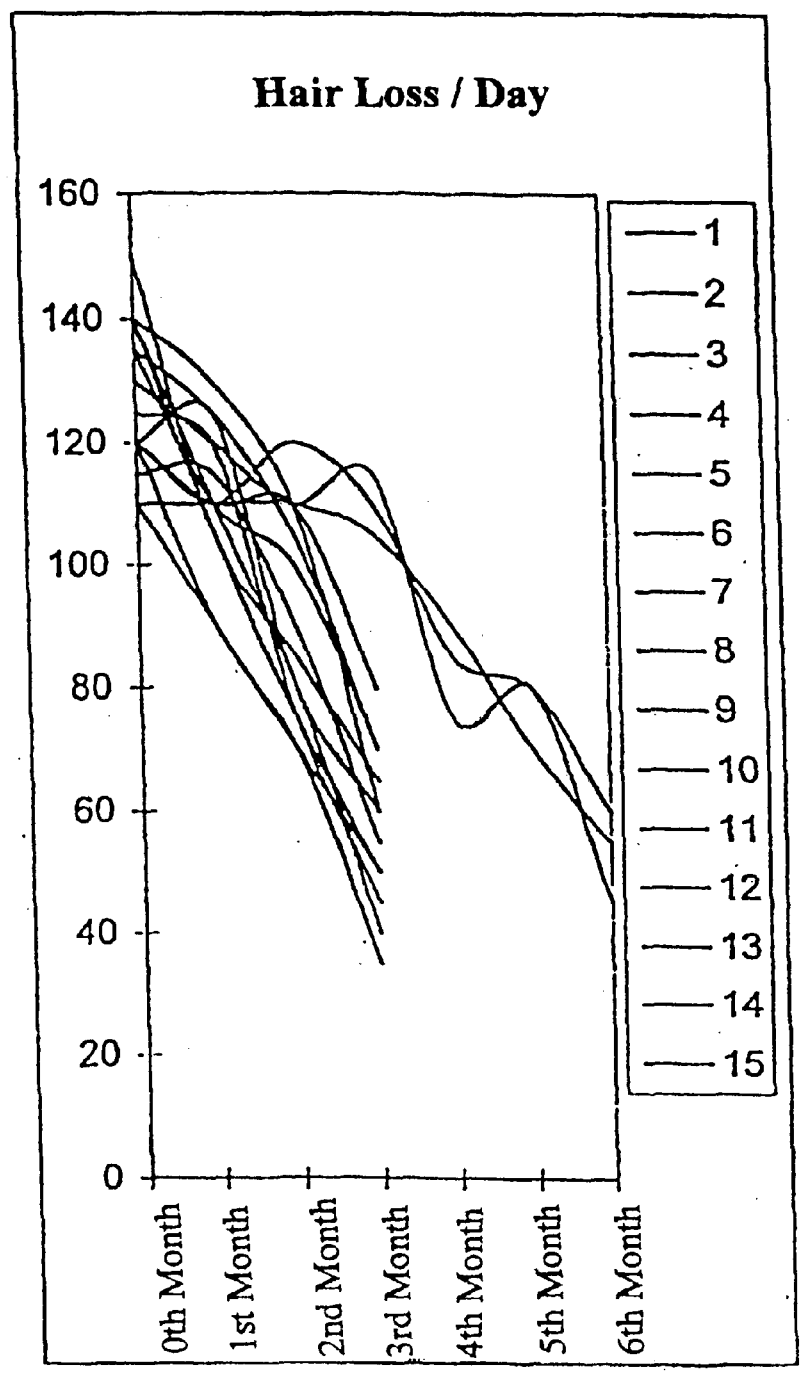

The present invention has as its object the creation of a physiological preparation that, by its special effect on the various energy metabolism pathways in the human and animal organism, as well as on the synthesis of structural proteins, has a crucial and more effective impact on the hair growth and the hair quality. The preparation of the present invention is exclusively administered orally and adapted to the individual needs of the treated person.

This object is accomplished with a preparation with the mixture specified in the characterizing part of claim 1.

Further advantageous developments of the invention are described in the dependent claims.

The invention will be described in more detail below, based on examples and six figures.

The invention is based on the surprising realization that the non-essential amino acid proline, which is characterized by its ring structure with a small space requirement, leads to a lasting intensification and acceleration of the protein biosynthesis of the main components of the hair, alpha-keratin and collagen, when it is combined with the branched-chain essential amino acids valine, isoleucine and/or leucine. Proline takes a special place among the amino acids. It is involved in the so-called alpha-helices of the proteins to a lesser degree than other amino acids, but it frequently occurs in the hair-pin shaped beta-loops and is therefore of special importance for the protein structure as "helix breaker".

The present invention uses a mixture of the four amino acids valine, leucine, isoleucine and proline. The percentages used in the mixture vary, depending on the purpose of the application, and they can also be excellently adapted to the individual needs of the patient. The four amino acids can be given alone, or supplemented with further amino acids such as cysteine, cystine, glycine, lysine, methionine, vitamins of the B-group such as biotin, as well as adenosine triphosphate. If an analysis prior to the treatment reveals a considerable deficiency in the trace or quantity elements calcium, chrome, iron, potassium, cobalt, copper, magnesium, manganese, molybdenum, sodium, nickel, phosphorus, selenium, vanadium or zinc, these can be added.

The U.S. application Ser. No. 51,984,465 describes, as mentioned above, an agent, which can be administered orally and serves to alleviate disorders of the collagen synthesis. Collagen is a protein similar to keratin, which forms the basic substance of the hair. In column 1, lines 45–47, it is mentioned that proline is probably the main limiting factor for the collagen synthesis due to its insufficient concentration in the plasma.

From this assumption it can be concluded that the keratin synthesis could also be disturbed by a proline deficiency and that a supplementation with proline might solve this problem.

The contribution of the present invention lies in having demonstrated, in the course of the conducted studies, that administering proline alone does not have an optimal effect.

An optimal effectiveness is reached, within the framework of the stated individual tolerances, only if it is administered in a mixture which also contains valine, leucine and isoleucine.

At proline dosages of over 80%, the effectiveness lessened noticeably in each studied case. Proline alone is thus not the main limiting factor for the synthesis of keratin and, probably, collagen. The necessary ratios of valine+isoleucine+leucine, at an optimal combined ratio of 20–62%, represent an equally important factor in the determination of the dosage as the optimal percentage of proline, which is 15–65%. The crucial factor is that the two factors individually are not able to produce an optimal effectiveness and have this effectiveness only when they are combined.

The application according to the invention of the amino acid mixture consisting of valine, leucine, isoleucine and proline, which may optionally be supplemented with further amino acids, vitamins and various elements as specified above, may have as a side effect a noticeable improvement of the various energy metabolism pathways, which furthermore has a positive effect on the patient's stamina, muscle tone, brain function, fat catabolism, blood fat and blood sugar values and firmness of the connective tissue. However, the preparation of the present invention contributes mainly and in an excellent way to a pronounced stimulation of the hair growth, as discussed above.

The preparation according to the invention may be administered orally in the form of powder, capsules, tablets or dissolved in liquid. Beside the active ingredients, the preparation may furthermore contain the usual auxiliary agents, carriers and additives. It may also be bound with fructose or sugar syrup, dried and processed into granules.

EXAMPLE 1

The following composition of the preparation according to the invention has proven particularly effective:

| Active Agent | Percentage | Preferably |
| --- | --- | --- |
| Cysteine | 0–10% | 2% |
| Glycine | 0–10% | 2% |
| Isoleucine | 5–25% | 15% |
| Lysine | 0–10% | 2% |
| Leucine | 10–40% | 22% |
| Proline | 4–60% | 40% |
| Valine | 5–20% | 11% |
| ATP | 0–10% | 1.9% |
| Biotin | 0–5% | 0.1% |

Twelve patients with hair growth disorders were given a combination of the four amino acids valine, leucine, isoleucine and proline daily for six months. In only 3 months' time, a noticeable improvement of the hair growth could be noted.

A control group of 3 patients was given the known combination of the three amino acids valine, leucine and isoleucine. After a three-month treatment no improvement of the hair growth disorder could be noted in these patients, and the treatment was therefore changed to the new combination of the four amino acids for this group as well. After a three-month treatment of the control group with the combination of the four amino acids, the hair growth disorders of these patients also improved noticeably, i.e., the daily hair loss was reduced (see FIGS. 1 and 2), the hair growth phases shifted from the katagenic and telogenic phase to the anagenic phase (see FIGS. 3 and 4), and the structure of the hair shafts improved noticeably as well (see FIGS. 5 and 6).

EXAMPLE 2

The following composition of the preparation according to the invention has proven particularly effective when adjusted individually to the respective hair and blood examinations of the male and female patients. It comprises a so-called basic preparation, a main supplement and an additional supplement:

| Active Ingredients | Percentage | For example |
| --- | --- | --- |
| Basic Preparation: | | |
| Isoleucine | 5–35% | 15% |
| Leucine | 10–50% | 23% |
| Proline | 5–65% | 33% |
| Valine | 5–30% | 11% |
| Main supplement to the basic preparation | | |
| ATP | 0–20% | 2% |
| Biotin | 0–5% | 1/4% |
| Cysteine | 0–20% | 2.75% |
| Cystine | 0–15% | 1.00% |
| Methionine | 0–15% | 1.50% |
| Additional supplement to the basic preparation | | |
| Glycine | 0–10% | 5% |
| Lysine | 0–10% | 5% |
| Taurine | 0–10% | 0.50% |

The present invention thus covers a dietetic preparation for the maintenance and/or regulation of the various energy metabolism pathways in the human and animal organism, for the intensification and acceleration of the protein biosynthesis, in particular for the main components of the hair, α-keratin and collagen, whereby an effective quantity of a mixture of the four amino acids valine, isoleucine, leucine and proline is administered orally.

The basic preparation according to example 2 can also serve as the basis for the mixture specified in example 1, and can be modified according to the individual needs of the patient as well as according to the symptoms to be treated.

If an analysis of the hair and the blood of a patient shows a deficiency in trace elements, the following elements can be added to the compositions specified in example 1 and 2:

| | | | |
| --- | --- | --- | --- |
| Potassium | (I-valent) | Sodium | (I-valent) |
| Calcium | (II-valent) | Iron | (II-valent) |
| Cobalt | (II-valent) | Copper | (II-valent) |
| Magnesium | (II-valent) | Manganese | (II-valent) |
| Molybdenum | (II-valent) | Nickel | (II-valent) |
| Selenium | (II-valent) | Vanadium | (II-valent) |
| Zinc | (II-valent) | Chrome | (III-valent) |
| Phosphorus (various valencies) | | | |

To improve the qualitative and quantitative hair growth, it is preferable to use a mixture of the amino acids valine to leucine to isoleucine in the ratio 7±20%:17±20%:11±20%, with the mixture additionally containing min./max. 4–80%, preferably 15–65% proline.

These four amino acids can be adapted to the individual requirements of the male and female patients by adding further amino acids, vitamins of the B-group, enzymes, fructose, adenosine triphosphate and trace elements, as described. The preparation according to the invention normalizes the hair loss, improves the hair quality, activates resting hair roots, and thereby results in a lasting improvement of the quantitative hair growth.

Figure 4:
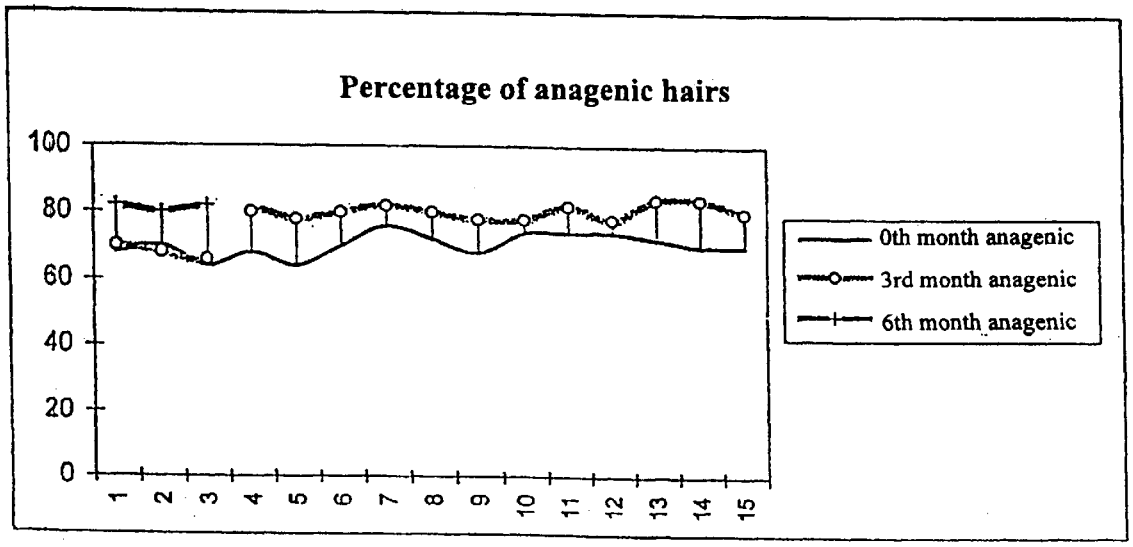
Figure 6:
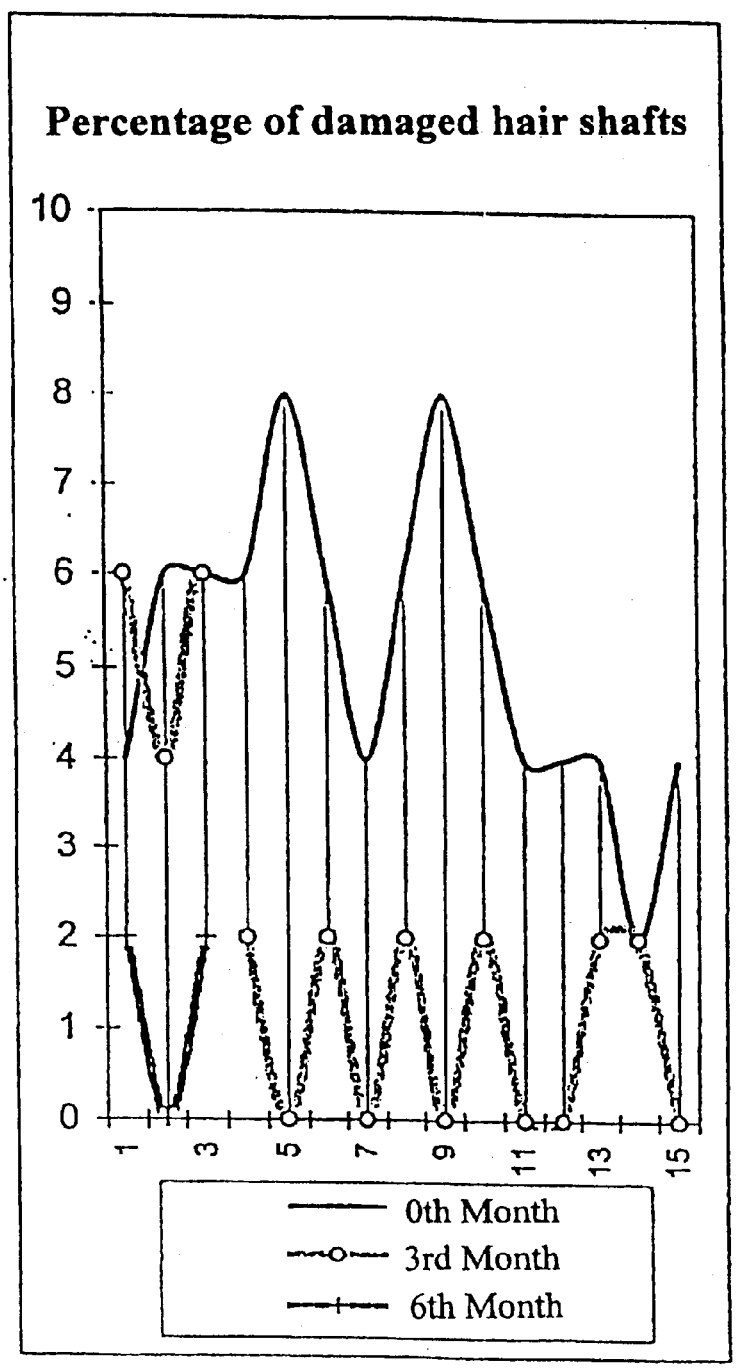

FIGS. 1 and 2 show a table and a diagram detailing the hair loss (number of hairs per day) of 15 patients; FIGS. 3 and 4 show the anagenic hair cycle phase in % (together with katagenic and telogenic=100%) and FIGS. 5 and 6 show the structure of the hair shaft (number of damaged hair shafts in %). The differentiation between the hair cycle phases was made by microscopic analysis (trichogram) of at least 50 extracted hairs (under normal conditions: anagenic phase= 80 to 85%).

While the composition according to example 1 has proven particularly effective for the treatment of hair growth disorders, the composition according to example 2 has proven particularly effective for the support of the various energy metabolisms in that a positive effect can be achieved regarding stamina, muscle build-up, brain performance, fat catabolism, blood fat values, blood sugar values, skin and hair regeneration, firmness of the connective tissue, fatigue and impaired potency.

To improve the qualitative and quantitative hair growth, skin structure and/or nail regeneration, it is preterable to use a mixture of the amino acids valine to leucine to isoleucine in the ratio 7±20%:17±20%:11±20%, with the mixture additionally containing proline.

What is claimed is:

1. A method for improving hair growth, skin structure and/or nail regeneration, comprising administering to a patient in need thereof a preparation comprising a mixture of amino acids, said mixture having a ratio of the amino acids valine to leucine to isoleucine of 7:17:11 plus/minus 20%, said mixture further comprising an effective amount of proline and at least one carrier.

2. The method according to claim 1, wherein said mixture comprises 22 wt. % valine, 44 wt. % leucine, 30 wt. % isoleucine and 4 wt. % proline.

3. The method according to claim 1, wherein said preparation further comprises at least one of the following amino acids up to 10 wt. % cysteine, up to 15 wt. % cystine, up to 10 wt. % glycine, up to 10 wt. % lysine, up to 15 wt. % methionine, up to 10 wt. % ATP and up to 5 wt. % biotin.

4. The method according to claim 1, wherein said preparation further comprises at least one of calcium, chrome, iron, potassium, cobalt, copper, magnesium, manganese, molybdenum, sodium, nickel, phosphorus, selenium, vandium and zinc.

5. The method according to claim 1, wherein said preparation is in an oral administration form of powder, tablets, capsules or as a soluble preparation.

6. The method according to claim 1, wherein said carrier comprises granules with sugar and/or fructose syrup.

7. The method of claim 1 wherein said effective amount of proline is 15–65 wt. %.

8. The method according to claim 1, wherein said preparation is in the form of at least two separate parts comprising
   a first part comprising 5–35% of said isoleucine, 10–50% by weight of said leucine, 5–65% of said proline and 5–30% of said valine, and
   a second part comprising ATP, biotin, cysteine, cystine and methionine, said ATP being present in an amount of up to 20%, said biotin being present in an amount up to 5%, said cysteine being present in an amount up to 20%, said cystine being present in an amount of up to 15% and said methionine being present in an amount or up to 15%.

9. The method of claim 8, further comprising administering a separate third part comprising glycine, lysine and taurine, each of said glycine, lysine and taurine being present in an amount of up to 10%.

10. A method for improving hair growth, comprising administering to a patient in need thereof a preparation comprising a mixture of amino acids, said mixture consisting essentially of more than 5 wt. % valine, more than 5 wt. % leucine, more than 5 wt. % isoleucine and more than 15 wt. % proline, and at least one carrier.

11. The method according to claim 10, wherein said mixture comprises 10–30 wt. % valine, 20–40 wt. % leucine, 15–35 wt. % isoleucine and 50–70 wt. % proline.

* * * * *